(12) United States Patent
Dai et al.

(10) Patent No.: US 6,974,035 B2
(45) Date of Patent: Dec. 13, 2005

(54) METHOD AND SYSTEM FOR PRODUCING A MOISTURE CONTENT MAP FOR USE IN MOISTURE SORTING GREEN VENEER USING LIGHT TRANSMISSION

(75) Inventors: Chunping Dai, Vancouver (CA); Tony Thomas, Richmond (CA); Kevin Groves, Delta (CA); Heng Xu, Vancouver (CA)

(73) Assignee: Forintek Canada Corp., Vancouver (CA)

( * ) Notice: Subject to any disclaimer, the term of this patent is extended or adjusted under 35 U.S.C. 154(b) by 201 days.

(21) Appl. No.: 10/418,080

(22) Filed: Apr. 18, 2003

(65) Prior Publication Data

US 2004/0206676 A1  Oct. 21, 2004

(51) Int. Cl.[7] ................................................ B07C 5/14
(52) U.S. Cl. ..................... 209/518; 209/577; 209/576
(58) Field of Search ............................... 209/517, 518, 209/576, 577

(56) References Cited

U.S. PATENT DOCUMENTS

| | | | |
|---|---|---|---|
| 3,812,964 A * | 5/1974 | Woodruff | 209/555 |
| 4,785,185 A | 11/1988 | Izatt et al. | |
| 4,905,843 A | 3/1990 | Holbert | |
| 5,006,225 A * | 4/1991 | Beauchemin et al. | 209/3.3 |
| 5,141,112 A * | 8/1992 | Holbert | 209/653 |
| 5,899,959 A | 5/1999 | Shields et al. | |
| 6,175,092 B1 * | 1/2001 | Binette et al. | 209/587 |
| 6,851,559 B2 * | 2/2005 | Kairi | 209/518 |

FOREIGN PATENT DOCUMENTS

| | | |
|---|---|---|
| EP | 0616209 A2 | 9/1994 |
| EP | 1287912 A1 | 3/2003 |

OTHER PUBLICATIONS

Sensortech Systems Inc. brochure entitled "ST-2200 Series On-Line Moisture Analysis", undated.

* cited by examiner

*Primary Examiner*—Donald P. Walsh
*Assistant Examiner*—Kaitlin Joerger
(74) *Attorney, Agent, or Firm*—Oyen Wiggs Green & Mutala LLP

(57) ABSTRACT

Disclosed is a method and system for sorting a plurality of green wood veneer sheets into a plurality of subsets of sheets, the subsets including a "driest" subset, a "wettest" subset, and one or more "intermediate" subsets. The system has a light source for transmitting light through a sheet of veneer as it passes along a conveyor system, and a light sensor for sensing the light passing through the sheet. The pattern of light is recorded by an image acquisition and processing subsystem as an image, which is fed to an image analysis subsystem programmed to analyse the light pattern and to produce a mathematical representation of the image. An integrated moisture content value (IMCV) is set for the particular veneer sheet. Based on this value, a controller sends signals to the conveyor system to convey the particular sheet to a location storing sheets having similar IMCV values for drying.

13 Claims, 5 Drawing Sheets

Fig.6: Sapwood-Heartwood Veneer

US 6,974,035 B2

METHOD AND SYSTEM FOR PRODUCING A MOISTURE CONTENT MAP FOR USE IN MOISTURE SORTING GREEN VENEER USING LIGHT TRANSMISSION

TECHNICAL FIELD

The present invention relates to methods and systems for sorting veneers, and in particular to methods of sorting green wood veneer sheets used in the manufacture of composite wood products such as plywood and laminated veneer lumber (LVL).

BACKGROUND

Plywood and other composite wood products such as LVL are produced from thin sheets of wood plies or veneers. To produce the veneer, logs are cut or peeled by sharp blades on a lathe or in other cutting machinery, producing a running ribbon or strip of veneer between one-tenth and one-quarter of an inch thick, depending on the type of plywood being made. The veneer strip is thereafter clipped to size, producing "green" or wet veneer sheets.

The green veneer sheets are dried in dryers, and glued together in layers to form a panel. Producing plywood or LVL from individual veneer sheets typically involves layering a plurality of glue-covered veneer sheets and then processing the sheets using a combination of pressure and heat to set the glue and fuse the veneer layers together.

It is important in the manufacturing process that the veneer sheets be dried to a relatively uniform moisture content, usually in the range of between 2–6% (this percentage figure being well known to those skilled in the art). The drying process stabilises the veneer dimension, strengthens the fibres, and prepares the wood for gluing. Mechanical driers are typically controlled by control of temperature, ventilation (to control humidity) and conveyer speed (to control time). In large modern driers, elaborate loading and unloading facilities are frequently provided.

It is important that the veneers not be too dry, nor too wet, or they will not bond well together. Further, if there are pockets of moisture, or areas of the veneer which are not dried to within the desired range, then "blows" can cause severe delamination in the finished plywood, which can result in product rejection.

Because the drying of the veneer sheets is such an important step in the manufacturing process, the veneer sheets are typically sorted into a plurality of subsets or "sorts" having approximately the same drying characteristics, ie. by species, thickness, heartwood or sapwood, and initial moisture content prior to drying. The driest green veneers are typically sorted together, as are the wettest, and the intermediate veneers may be sorted into one or more intermediate sorts.

The driest veneers are dried together as a batch for a certain period of time and/or at a certain temperature or humidity level to achieve the desired end moisture content. Similarly, the wettest sort is dried together (for a longer period of time, and/or at a different temperature and humidity) to achieve a relatively similar end moisture content. The intermediate sort(s) are dried for some intermediate time, and/or at another different temperature and/or humidity.

Therefore, veneer drying is a very important aspect of production of wood composite products from veneers, and moreover, veneer sorting is a very important factor relating to drying. One continuing problem in sorting green veneer, however, relates to the determination of its initial moisture content in determining which "sort" a particular sheet should be directed to.

It has been the case in the past that the relative sort point of moisture content of a particular sheet of green veneer will simply be estimated by a human operator of a sorting system. After years of experience, an operator may have the skill to roughly sort sheets into appropriate subsets, knowing the species of the wood being dried and its thickness, by knowing whether the sheet comes from sapwood or heartwood, and by looking at the sheet as it passes downstream from the cutting apparatus. Unfortunately, the human operator has little time to see the sheet in a typical fast-moving system, and it is not uncommon for sheets to be misdirected into inappropriate sorts, even by the most experienced operator.

The problem with inappropriately directing sheets into the wrong sort is that if the sheet is dried for a longer period of time than necessary to reach the desired moisture content, bonding sites on the surface of the veneer can be destroyed or deactivated, thus creating bonding problems between plies. If the sheet is dried for a shorter period of time than necessary, it will still be too wet to use.

In a typical mill which relies on an operator's expertise in judging the initial moisture content of veneer sheets, it is more typical (and indeed prudent to avoid wastage from over drying) that the operator will direct a sheet to a "shorter time" sort than would be more appropriate (ie. a wet sheet will be placed inappropriately in a sort which is not dried for very long). This avoids over drying, but it does not allow the sheet to dry to the desired moisture in one pass through the dryer. All sheets are checked for moisture content after they are dried, and the wet ones are returned to the dryer as "re-dries". An operator will adjust the variables in the drying system during the drying process to try to reduce the amount of "re-dry" iteratively: when too many sheets come out of the dryer still wet, the operator adjusts the time, temperature and humidity to reduce the percentage of "re-dries" for the remainder of the sheets in the batch.

However, even with this iterative intervention by a human operator, the percentage of "re-dry" in a typical veneer drying system is quite high, and this leads to increased costs of production in increased machine time, increased operator time, and increased energy usage.

It is important, therefore, to try to reduce the amount of re-dry in a veneer drying system. To reduce the amount of re-dry, it would be desirable to place certain sheets which would otherwise end up out of the drier as re-dry into a sort which has wetter sheets in it (to subject the sheet to a longer drying time, or higher temperature or lower humidity). For this, it would be useful to have a good understanding of the nature of the initial moisture content of the veneer sheet.

Attempts have been made in the past to better measure the initial moisture content of green veneer sheets, in an effort to minimize the effect of the necessity for human intervention in the sorting process. For example, certain attempts have been made to determine the moisture content of a veneer sheet by measuring the electrical or dielectrical properties of the wood. It has been found, however, that the sensors used for this purpose are accurate only when the moisture content is low (ie. below 30%).

Most commonly today, there are also Radio Frequency-based ("RF") sensor systems in use. These sensors use radio frequencies to measure moisture content of sheets of veneer. They too, however, are not accurate at higher moisture ranges (perhaps >70%), but more importantly, RF sensors are highly sensitive to operating conditions. The accuracy of RF sensor measurements are significantly affected by veneer shape and flatness, and by wood grain angle, and by the distance between the RF source and the face of the veneer sheet. Small distance changes (in the order of a millimetre or two, or even less) between the RF source and sensor head and the sheet face cause large variations in readings. In most drying and sorting systems, veneer sheets are moved along conveyors rapidly and "bounce" along the conveyor such that there are widely varying distances between the sheet and the RF sensor head as the sheet passes the sensor head, leading to erroneous readings.

There remains a need, therefore, for a better system for sorting green veneer more appropriately and more accurately into sorts or subsets for drying in a dryer, thereby reducing the re-dry amount and increasing productivity, reducing energy consumption, and providing better quality dried veneer for use in plywood. The inventors believe that the key to this desired system is improved moisture measurement accuracy.

SUMMARY OF INVENTION

The present invention provides a method and system for sorting veneers, and in particular a method and system for sorting green wood veneers used in the manufacture of composite wood products such as plywood and laminated veneer lumber (LVL). A moisture content map is produced representative of the moisture within an article of wood. One key aspect of the invention is the determination by the inventors that the green veneer moisture content is correlated with the amount of light able to pass through a sheet of veneer.

At its most basic, the invention comprises a method of producing a moisture content map representative of the moisture within an article of wood. To produce this map, light is directed from a light source onto one face of the article of wood. The light intensity pattern of the light passing through the article of wood is sensed by a light sensor facing the opposite face of said article of wood. The light intensity pattern is then recorded as an image, or some other collection of data. The image is then provided to image analysis software provided in a data processor, and processed to produce a mathematical representation of the image.

In one embodiment of the invention, a method is provided for sorting a plurality of green wood veneer sheets into a plurality of subsets of sheets, the subsets including a "driest" subset, a "wettest" subset, and one or more "intermediate" subsets, the method comprising the steps of: for each one of the sheets, producing a moisture content map; providing an analysis of the moisture content map; from the analysis of the moisture content map determining which one of the subsets the sheet should be placed into; and conveying the sheet to a storage location storing the one of the subsets of sheets.

In the preferred embodiment of the invention, the moisture content map is produced by: directing light from a light source onto one face of the sheet; sensing the light intensity pattern of the light passing through the sheet with a light sensor facing the opposite face of the sheet; recording the light intensity pattern as an image; providing the image to image analysis software provided in a data processor; and processing the image with the image analysis software to produce a mathematical representation of the image.

The present method may be carried out by a system comprising a conveyor subsystem for conveying each one of the plurality of veneer sheets from an initial location to one of the subsets; a light source for directing light onto one face of each one of the sheets as it is conveyed from the initial location to the subset; a light sensor facing the opposite face of the sheet for sensing the light intensity pattern of the light passing through the sheet facing the opposite face of the sheet; an image acquisition and processing subsystem for recording the light intensity pattern as an image; an image analysis subsystem for accepting the image from the image processing subsystem and for analysing the image, the analysis subsystem generating an output signal dependent upon the analysis of the image, each output signal generated by the analysis system relating to only one of the subsets; and a control system to accept the signal produced by the analysis subsystem and to direct the conveyor system to convey the sheet to a storage location storing the one of the subsets of sheets.

BRIEF DESCRIPTION OF DRAWINGS

In the accompanying drawings which illustrate specific embodiments of the invention, but which should not be construed as restricting the spirit or scope of the invention in any way.

DESCRIPTION

Throughout the following description, specific details are set forth in order to provide a more thorough understanding of the invention. However, the invention may be practised without these particulars. In other instances, well known elements have not been shown or described in detail to avoid unnecessarily obscuring the invention. Accordingly, the specification and drawings are to be regarded in an illustrative, rather than a restrictive, sense.

Figure 1:
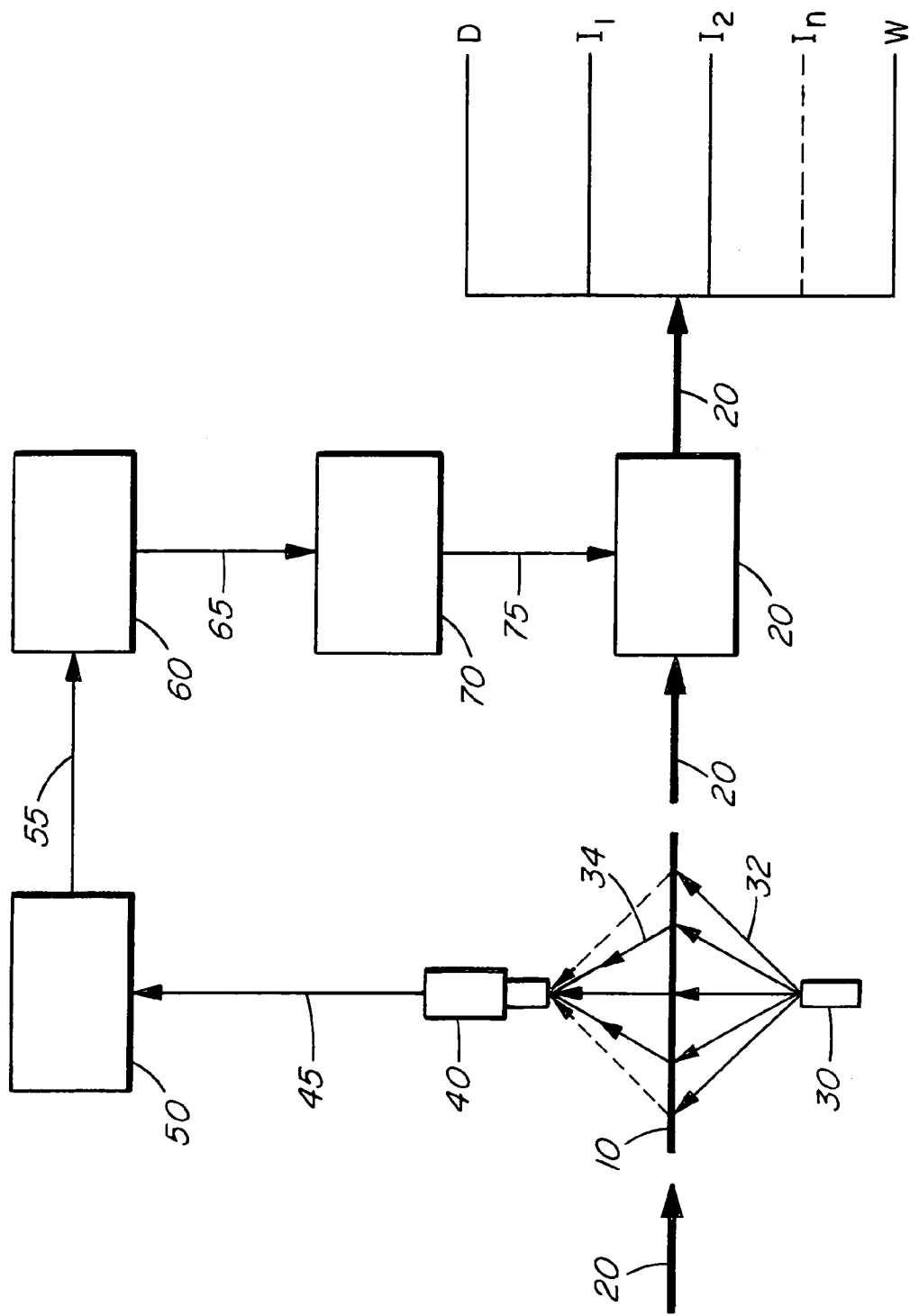
FIG. 1 is a schematic plan view of the system of the present invention.

Referring first to FIG. 1, a preferred system for implementing the method of the present invention includes a traditional veneer sheet conveyor system 20 which might be found in a typical veneer sorting system in a plywood mill. Such a system typically conveys cut veneer sheets 10 to sorting piles in accordance with the dictates of a human operator, working on his own or with the assistance of surface moisture measurements from a Radio Frequency (RF) moisture measuring system, as well known in the art.

In the present system, however, the conveyor system 20 conveys a sheet of veneer 10 to a position between a light source 30, and a light sensor 40 for a certain period of time, rather than subjecting sheet 10 to RF sensing.

In the preferred embodiment, light source 30 emits light 32, preferably but not necessarily visible light, towards one face of veneer sheet 10. Light source 30 may have a single light-producing element or may have a plurality of elements which may be centrally located near the center of the face of sheet 10, or which may be spaced apart and directed at different areas of the sheet's face. A certain fraction of emitted light 32 passes through sheet 10 as transmitted light 34. Transmitted light 34 is sensed by light sensor 40, which in a preferred embodiment is appropriately positioned on the opposite side of sheet 10 to capture the pattern of transmitted light 34.

Light sensor 40 sends signals 45 to an image acquisition and processing subsystem 50. Image processing subsystem 50 produces an image such as that shown in FIGS. 2–6, and thereafter provides the image to an image analysis subsystem 60 by way of signal 55.

Figure 2:
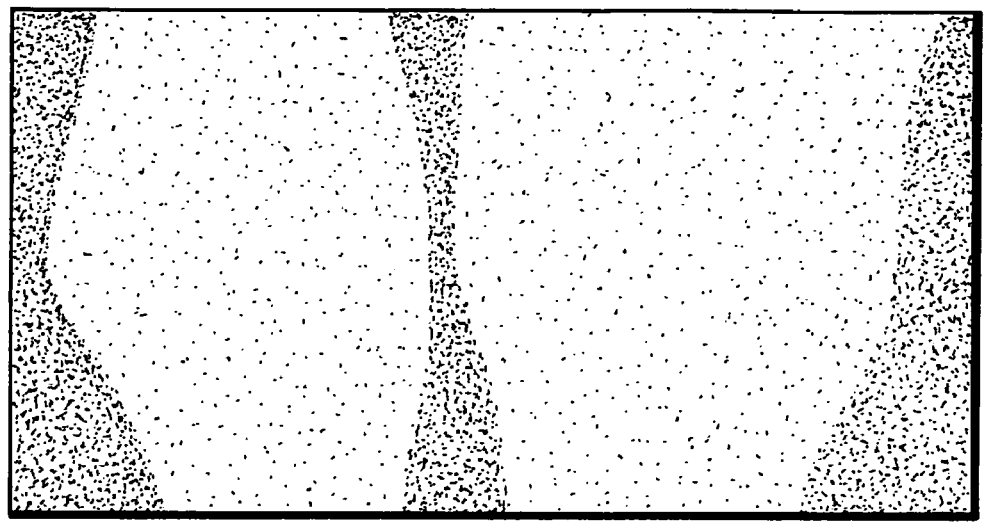
FIG. 2 is a schematic view of an image produced by the system shown in FIG. 1, for a relatively wet sheet of veneer.
Figure 3:
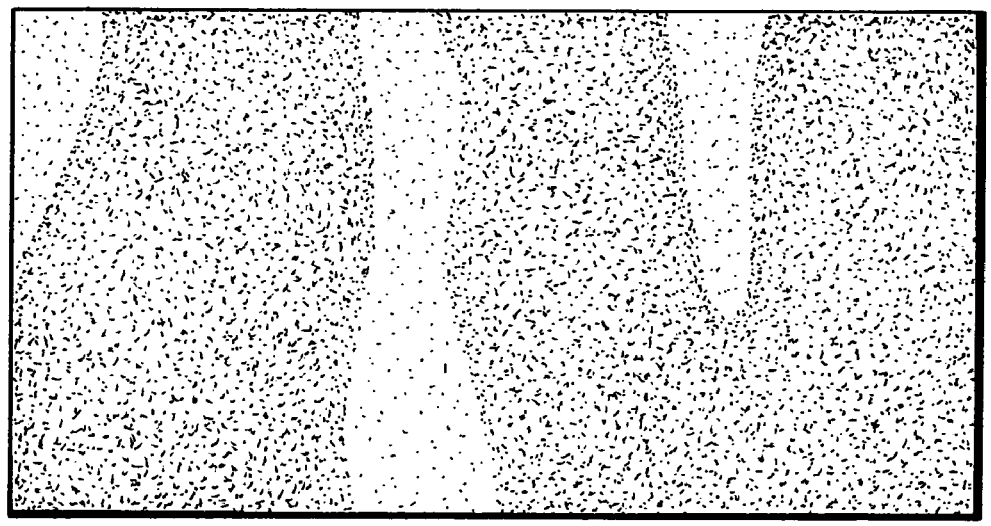
FIG. 3 is a schematic view of an image produced by the system shown in FIG. 1, for a relatively dry sheet of veneer.
Figure 4:
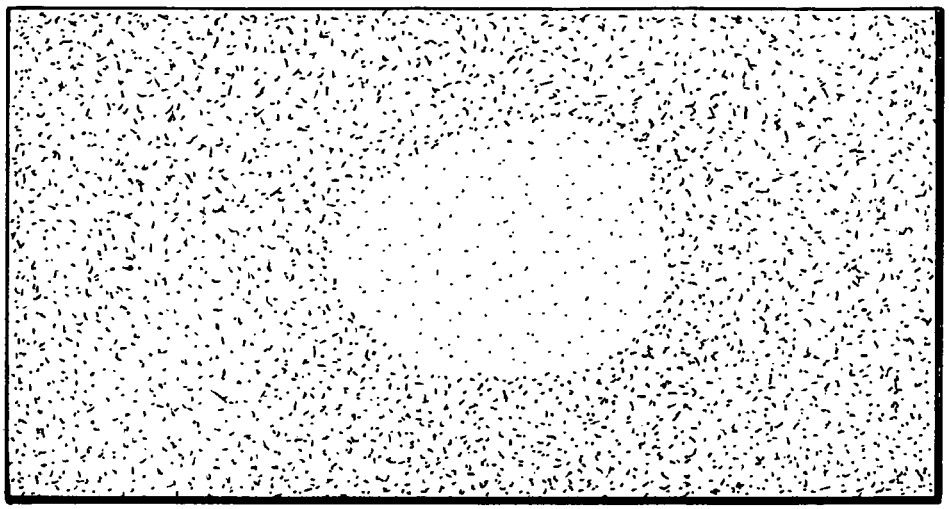
FIG. 4 is a schematic view of an image produced by the system shown in FIG. 1, for a relatively dry sheet of veneer having a single large wet area.
Figure 5:
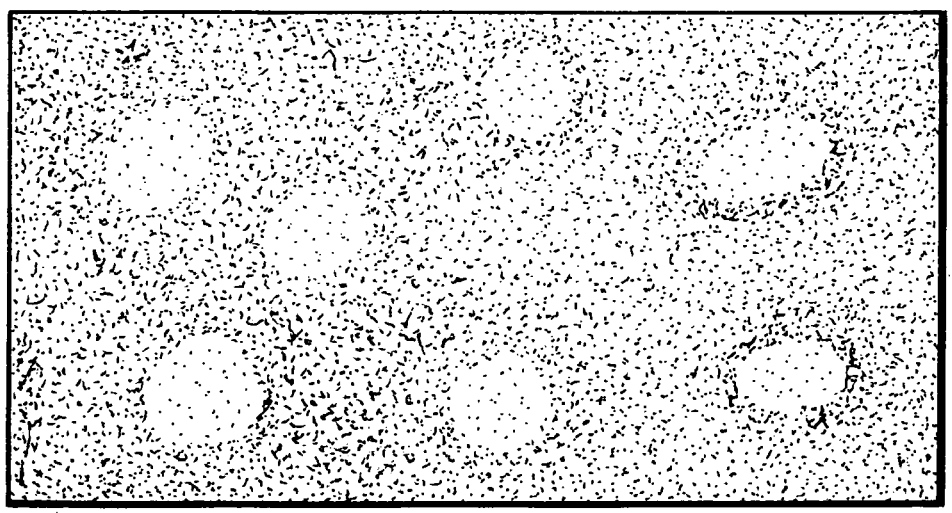
FIG. 5 is a schematic view of an image produced by the system shown in FIG. 1, for a relatively dry sheet of veneer having a number of small wet areas.
Figure 6:
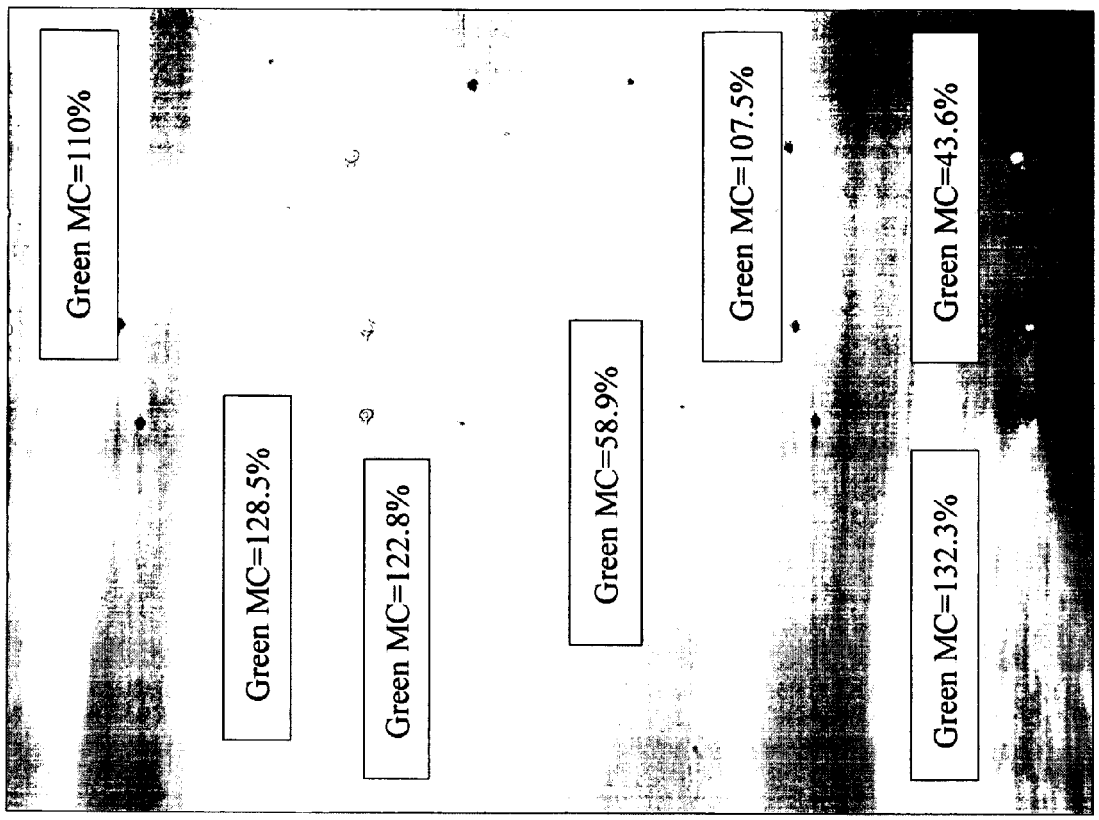
FIG. 6 is an actual image of a sheet of green veneer, produced in accordance with the system and method of the present invention.

The inventors have determined that for two similar pieces of green veneer, (ie. two sheets of the same species of wood, and of the same thickness), there is a strong correlation between the moisture content and the amount of light able to be transmitted therethrough. The "transmittance" of a wet sheet of veneer is in fact greater than that of a dry piece of veneer (the dry piece is more opaque). It is readily apparent, then, that sensor 40 will sense more light passing through a wet sheet of veneer than a dry sheet. In a preferred embodiment, the image produced by image processing subsystem 50 will reflect relative dryness as "dark", and wetness as "light". To illustrate this, FIG. 2 shows a relatively "wet" sheet of veneer, while FIG. 3 shows a relatively "dry" sheet. Of course, it is not necessary that "wet" be shown in the image as "dark" for the system to be employed; it is foreseen that system 50 could also produce a negative of this image.

It is well known, moreover, that veneer sheets are seldom uniform in moisture content throughout their volume, and that sheets have areas which are wetter than others. This can be reflected in the image produced by image processing subsystem 50. In this way, the image can show the 2-dimensional area distribution of the moisture content in the sheet.

The fact that the light transmittance of the veneer sheet increases when the sheet is wet allows the image analysis subsystem 60 to produce a "moisture content map" from the image received from image acquisition and processing subsystem 50. The map corresponds to the image and shows, mathematically, where areas of relative moisture are contained within the sheet 10 and their general size. By means of analysis of the "relative darkness" of areas of the image, the relative moisture of different areas of the sheet (and preferably, of the entirety of the sheet) can also be accounted for.

The mathematical representation of relative moisture of certain areas of the sheet, and of the sheet as a whole, allows the analysis subsystem 60 to compute what might be termed an "integrated moisture content value" (IMCV) for each sheet. The IMCV will not necessarily reflect the "average" moisture content of each sheet, but will also take into account the relative size and position of pockets of moisture. For example, while certain means for determining average moisture (for example, RF means, or human means) might consider the sheets of FIGS. 4 and 5 to be roughly equal in overall moisture, the sheet of FIG. 4 will be required to be dried longer than that of FIG. 5, since the one single wet area of the sheet of FIG. 4 will take longer to dry than the many smaller areas of the sheet of FIG. 5.

It will be appreciated that subsystem 60 may be programmed to take into account variables such as wood species, veneer thickness, the presence of knots and knot holes, and other variables which affect the light transmitting properties of the sheet of veneer.

By way of illustration, it may be the case that image analysis subsystem 60 is programmed to compute IMCV's having values of between 0 and 100. For each sheet, this value is transmitted to a control 70 by way of a signal 65, which is programmed to instruct conveyer 20 to convey the particular sheet to an appropriate sorting location. As shown in FIG. 1, the "driest" 25% of the sheets (perhaps those having IMCV values of 1–25, only by way of illustration) might be directed to the "D" sort (driest sheets), those sheets having IMCV values of between 26–50 are directed to sort $I_1$, those sheets having IMCV values of between 51–75 are directed to sort $I_2$, and those having IMCV values of between 76–100 are directed to the "W" (wettest sheets) sort. Any suitable number of intermediate sorts $I_n$, may be employed in the system, each sort containing sheets having a predetermined range of IMCV values.

It will be appreciated that the analysis of the moisture content map will require inputs regarding wood species, veneer thickness, and other similar variables. However, image analysis subsystem 60 can easily be programmed with these variables by someone skilled in the art.

Figure 7:
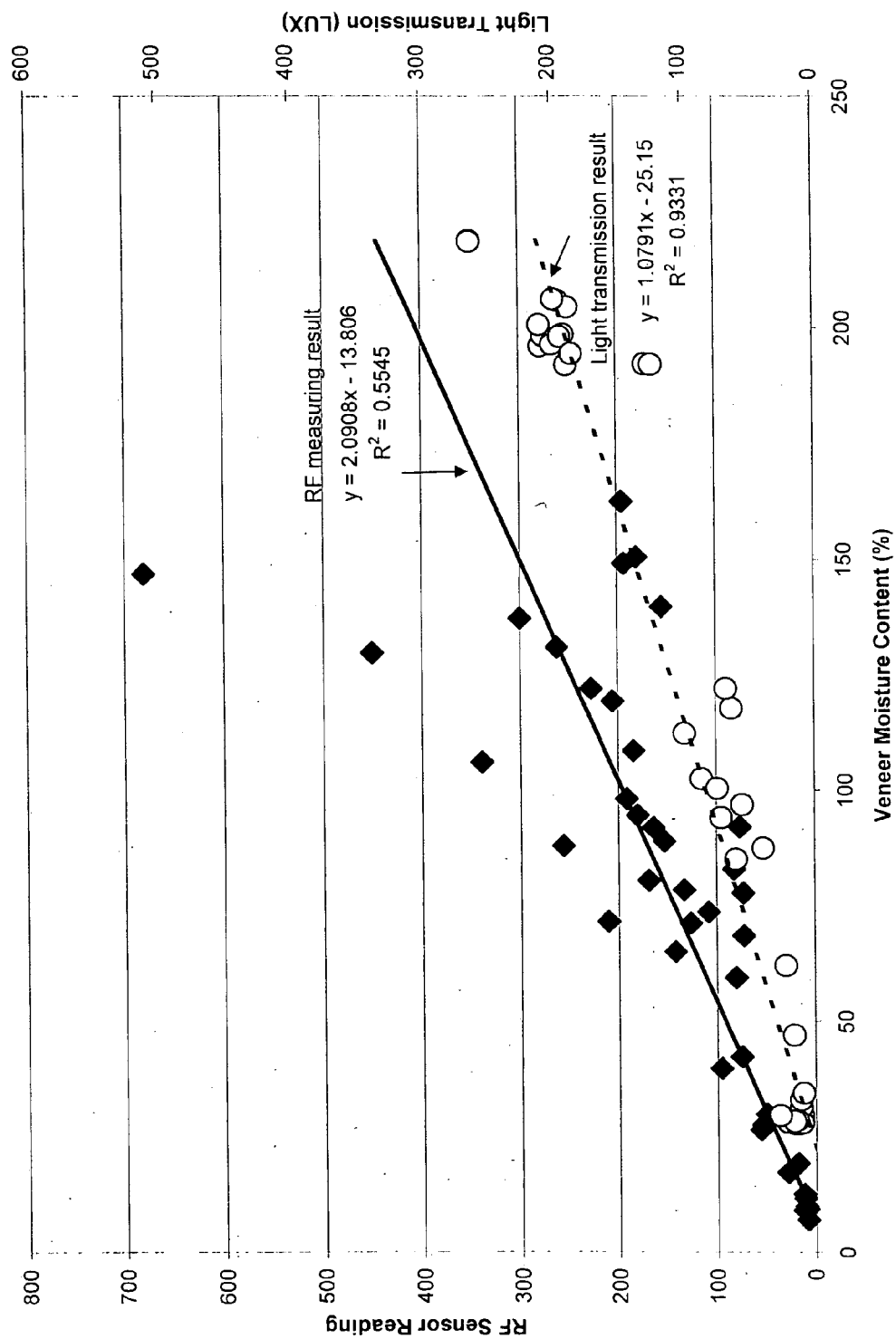
FIG. 7 is a graph showing plots of moisture readings for green veneer taken both with an RF sensor and also determined by the method of the present invention, compared to actual oven dry moisture content.

The benefits of the system for improving the measurement of moisture content of veneer (and thus improving the sorting of the veneer) are illustrated by the experimental results shown in FIG. 7. This figure shows, as a function of oven dry veneer moisture content, moisture content figures as determined by an RF sensor system and also by the present invention. As known in the art, the oven dry moisture content (or what might be termed "true" moisture content) values are determined, essentially, by calculating the ratio of the mass of a wet sheet of veneer to its mass after oven drying, minus 100%. It can be readily seen that the measurements taken by the RF sensor vary more widely (where $R^2=0.5545$) from the "true" moisture content values than do those taken with the system of the present invention (where $R^2=0.9331$). The readings taken with the system of the present invention correlate highly with the "true" moisture content values.

As will be apparent to those skilled in the art in the light of the foregoing disclosure, many alterations and modifications are possible in the practice of this invention without departing from the spirit or scope thereof. For example, it is contemplated that the sheet 10 may be stationary when light 32 is passed through it, but need not be. Further, the light source may be artificial, but need not be. As another example, any photo detector array may be used to detect the light passing through the veneer sheet.

Accordingly, the scope of the invention is to be construed in accordance with the substance defined by the following claims.

What is claimed is:

1. A method for sorting a plurality of green wood veneer sheets into a plurality of subsets of sheets, the subsets including a "driest" subset, a "wettest" subset, and one or more "intermediate" subsets, the method comprising the steps of:

for each one of said sheets, producing a moisture content map;

providing an analysis of said moisture content map;

from said analysis of said moisture content map, determining which one of said subsets said sheet should be placed into; and providing a signal to a conveying system to convey said sheet to a storage location storing said one of said subsets of sheets.

2. The method of claim 1 further comprising the final step of conveying said sheet to a storage location storing said one of said subsets of sheets.

3. A method of producing a moisture content map representative of the moisture within an article of wood, comprising the steps of:
- directing light from a light source onto one face of said article of wood;
- sensing the light intensity pattern of the light passing through said article of wood with a light sensor facing the opposite face of said article of wood;
- recording said light intensity pattern as an image;
- providing said image to image analysis software provided in a data processor; and
- processing said image with said image analysis software to produce a mathematical representation of said image.

4. The method of claim 2 wherein said moisture content map is produced by:
- directing light from a light source onto one face of said sheet;
- sensing the light intensity pattern of the light passing through said sheet with a light sensor facing the opposite face of said sheet;
- recording said light intensity pattern as an image;
- providing said image to image analysis software provided in a data processor; and
- processing said image with said image analysis software to produce a mathematical representation of said image.

5. The method of claim 4 further comprising sending a signal based on said moisture content map to a control system from said image analysis software, said control system controlling said conveyor system for conveying said sheet to the appropriate one of said subsets of sheets.

6. A method for sorting a plurality of green wood veneer sheets into a plurality of subsets of sheets, the subsets including a "driest" subset, a "wettest" subset, and one or more "intermediate" subsets, the method comprising the steps of:
- for each one of said sheets,
- directing light from a light source onto one face of said sheet;
- sensing the light intensity pattern of the light passing through said sheet with a light sensor facing the opposite face of said sheet;
- recording said light intensity pattern as an image with an image acquisition and processing subsystem;
- providing said image to an image analysis subsystem;
- providing a signal generated by said image analysis subsystem in response to said image to a control system programmed to control a conveyor system to convey said sheet to a storage location storing said one of said subsets of sheets.

7. A system for sorting a plurality of green wood veneer sheets into a plurality of subsets of sheets, the subsets including a "driest" subset, a "wettest" subset, and one or more "intermediate" subsets, the system comprising:
- a conveyor subsystem for conveying each one of said plurality of veneer sheets from an initial location to one of said subsets;
- a light source for directing light onto one face of each one of said sheets as it is conveyed from said initial location to said subset;
- a light sensor facing the opposite face of said sheet for sensing the light intensity pattern of the light passing through said sheet facing the opposite face of said sheet;
- an image acquisition and processing subsystem for recording said light intensity pattern as an image;
- an image analysis subsystem for accepting said image from said image processing subsystem and for analysing said image, said analysis subsystem generating an output signal dependent upon the analysis of said image, each output signal generated by said analysis system relating to only one of said subsets; and
- a control system to accept said signal produced by said analysis subsystem and to direct said conveyor system to convey said sheet to a storage location storing said one of said subsets of sheets.

8. The system of claim 7 wherein said light sensor and said image acquisition and processing subsystem are integrated into a camera.

9. The system of claim 8 wherein said camera is a digital camera.

10. The system of claim 7 wherein said image analysis subsystem is incorporated within said control system.

11. The method of claim 2 wherein said light source provides visible light and wherein the steps of sensing the light intensity pattern and recording the light intensity pattern as an image are accomplished by a camera.

12. The method of claim 2 or the system of claim 7 wherein there exists one intermediate sort.

13. The method of claim 2 or the system of claim 7 wherein there exist two intermediate sorts.

* * * * *